United States Patent [19]
Hutton

[11] Patent Number: 5,688,451
[45] Date of Patent: Nov. 18, 1997

[54] METHOD OF FORMING AN ABSORBABLE BIOCOMPATIBLE SUTURE YARN

[75] Inventor: Jeffrey D. Hutton, Southbury, Conn.

[73] Assignee: American Cyanamid Company, Wayne, N.J.

[21] Appl. No.: 726,969

[22] Filed: Oct. 7, 1996

Related U.S. Application Data

[63] Continuation of Ser. No. 367,880, Jan. 3, 1995, abandoned.

[51] Int. Cl.⁶ ............................ D01D 5/16; D02J 1/08
[52] U.S. Cl. ............................ 264/103; 28/104; 264/130; 264/210.3; 264/210.8; 264/211.14
[58] Field of Search ....................... 264/103, 130, 264/210.3, 210.8, 211.14; 28/104; 57/310, 350, 908

[56] References Cited

U.S. PATENT DOCUMENTS

| | | | |
|---|---|---|---|
| 3,297,033 | 1/1967 | Schmitt et al. | 606/230 |
| 3,371,713 | 3/1968 | Lachapelle et al. | 139/452 |
| 3,620,666 | 11/1971 | Lenz et al. | 8/130.1 |
| 3,766,872 | 10/1973 | Krieger | 112/439 |
| 3,791,388 | 2/1974 | Hunter et al. | 606/229 |
| 3,803,282 | 4/1974 | Hamana et al. | 264/103 |
| 3,807,273 | 4/1974 | Kurtz et al. | 57/310 X |
| 3,839,297 | 10/1974 | Wasserman et al. | 528/357 |
| 4,003,974 | 1/1977 | Chantry et al. | 264/210.8 |
| 4,027,676 | 6/1977 | Mattei | 606/230 |
| 4,096,226 | 6/1978 | Martin et al. | 264/168 |
| 4,621,638 | 11/1986 | Silvestrini | 606/230 |
| 4,648,240 | 3/1987 | Hallsworth et al. | 57/288 |
| 5,066,439 | 11/1991 | Nishikawa et al. | 264/103 |
| 5,069,846 | 12/1991 | Grindstaff et al. | 264/103 |
| 5,087,401 | 2/1992 | Yokoyama et al. | 264/130 |
| 5,102,419 | 4/1992 | Gertzman et al. | 606/228 |
| 5,232,648 | 8/1993 | Kennedy et al. | 264/210.8 |
| 5,275,618 | 1/1994 | Koyfman et al. | 606/228 |
| 5,288,516 | 2/1994 | Anderson et al. | 427/171 |
| 5,292,328 | 3/1994 | Hain et al. | 264/210.8 X |
| 5,294,395 | 3/1994 | Broyer | 264/178 F |

OTHER PUBLICATIONS

E.R. Kaswell, "Yarn Manufacturing", Wellington Sears Handbook of Industrial Textiles, p. 95 (1963).

*Primary Examiner*—Leo B. Tentoni
*Attorney, Agent, or Firm*—Fitzpatrick, Cella, Harper & Scinto

[57] ABSTRACT

A process for producing an absorbable biocompatible medical suture yarn includes the step of spin drawing a bioabsorbable polymer to form suture filaments. A spin finish using a non-aqueous based carrier is applied to the filaments during processing, and an air entangling step is used after the filaments are combined to form the suture yarn.

16 Claims, 4 Drawing Sheets

METHOD OF FORMING AN ABSORBABLE BIOCOMPATIBLE SUTURE YARN

This application is a continuation-in-part of application Ser. No. 08/367,880, filed Jan. 3, 1995, now abandoned.

BACKGROUND OF THE INVENTION

1. Field of the Invention

This invention relates generally to a method of forming a suture yarn for use in medical sutures and to the formed suture yarn itself. More particularly, the invention relates to a method of making an absorbable, biocompatible suture yarn from a bioabsorbable polymer.

2. Description of the Prior Art

Sutures for use in the medical field are predominantly multi-filament structures formed by twisting together, braiding or otherwise combining a plurality of filaments. Typically speaking, a predetermined number of filaments are combined together to form a suture yarn, and a plurality of suture yarns are braided or twisted together to form the medical suture. In an alterative arrangement, a core suture yarn is wrapped in sheath yarns to form the medical suture by either braiding or twisting.

Although monofilament sutures are popular, multi-filament sutures have been found generally to provide better tensile strength, knotting strength and other beneficial handling characteristics. The individual filaments are generally fabricated from a polymeric resin, and are optimally formed by extrusion from a polymer melt.

A highly desirable polymer for use in forming the individual filaments is poly(glycolic acid) (PGA). Filaments extruded from PGA are bioabsorbable and biocompatible, and therefore can safely be absorbed into the body after a relatively short time period, making it unnecessary for the sutures to be removed from the patient. One example of an absorbable suture made of a PGA polymer can be found in U.S. Pat. No. 4,621,638.

Producing multi-filament suture yarn is conventionally done using a two-step extrusion process. In the first step the melted polymer is extruded using known melt-spinning techniques to produce yarns having low orientation. These yarns are subsequently draw-twisted in a second, off-line step whereby the fibers are drawn to strengthen the filaments and then the filaments are twisted to form a cohesive suture yarn. U.S. Pat. No. 5,102,419 shows one example of forming surgical sutures using this conventional two-step extrusion process. U.S. Pat. No. 5,232,648 forms multi-filament, bioabsorbable sutures using a two-step extrusion process and discloses data of the melt-spinning conditions for forming the fibers and drawing conditions for drawing the fibers into surgical filaments.

U.S. Pat. No. 5,294,395 discloses an extrusion process and a redrawing process to form a thermoplastic monofilament suture. However, because of their relatively large diameters, monofilament sutures are drawn at much slower speeds than multi-filament sutures. In addition, as a result of the larger size of the monofilament sutures, the extrusion process in U.S. Pat. No. 5,294,395 uses a liquid quenching tank and heaters disposed between the drawing rolls. For at least these reasons, equipment for producing monofilament sutures is inappropriate for producing multi-filament suture yarns.

Although a continuous spin drawing process has been used for many years to produce industrial fibers, using such a one-step extrusion process with a PGA polymer is heretofore unknown. In a conventional spin drawing process, a polyethylene terephthalate (PET) or other comparable resin is used to form synthetic multi-filament yarns for use in, for example, carpets or ropes. For a detailed discussion of this process, reference is made to U.S. Pat. No. 3,803,282, or U.S. Pat. No. 4,003,974. These patents, however, do not contemplate using an absorbable, biocompatible polymer resin such as PGA, and therefore fail to improve upon known methods for manufacturing absorbable medical sutures.

SUMMARY OF THE INVENTION

It is a principal object of the present invention to provide an improved method of producing absorbable, biocompatible suture yarn.

Accordingly, one object of the invention is to provide a high output method of producing surgical yarn made of a bioabsorbable polymer such as poly(glycolic acid) (PGA).

It is another object of the invention to melt extrude a bioabsorbable polymer into filaments using a one-step spin drawing process.

It is another object of the invention to use a finishing solution that will not breakdown the absorbable suture yarn.

It is still another object of the invention to use an air entanglement process for making a multi-filament suture yarn.

It is yet another object of the invention to form an absorbable, biocompatible suture yarn of a PGA material using a spin drawing process.

In accordance with one aspect of the invention, a method of forming absorbable, biocompatible suture filaments comprises the steps of melt extruding a bioabsorbable polymer such as PGA to form filaments, and drawing the filaments in a continuous step.

In accordance with another aspect of the invention, a method of forming an absorbable, biocompatible suture yarn comprises the steps of melt extruding a bioabsorbable polymer to form a plurality of surgical filaments, drawing the extruded filaments in a continuous step, combining the drawn filaments into a parallel continuous arrangement to form a yarn, and securing the filaments together to stabilize the yarn.

In another aspect of the invention, the combined filaments are fed through an entangler to secure the filaments together.

In yet another aspect of the invention, the surgical filaments are treated with a finishing solution having a lubricant and an anti-static agent in a non-aqueous-based carrier.

These and other objects, aspects, features and advantages of the present invention will become apparent from the following detailed description of the preferred embodiments taken in conjunction with the accompanying drawings.

DESCRIPTION OF THE PREFERRED EMBODIMENTS

The suture yarn produced by the disclosed method is formed from a bioabsorbable polymer. While the embodiment disclosed below uses a poly(glycolic acid) (PGA) in forming the filaments, bioabsorbable polymers such as, for example, glycolide, lactide, caprolactone, p-dioxanone, trimethylene carbonate and physical and chemical combinations thereof can be used without departing from the scope of the subject invention.

Extruded PGA polymer yields an absorbable, biocompatible filament ideally suited for use as a suture yarn. The PGA suture safely breaks down in the patient's body after a time period sufficient for the sutured tissue (for example) to heal. The PGA polymer used in the spin drawing process preferably has an inherent viscosity at 30° C. of between 0.9 dl/g and 1.2 dl/g as measured in a solvent of hexafluoroacetone sesquihydrate, with a concentration of polymer in the solvent of 0.5% w/v. The moisture content of the polymer prior to extrusion is less than 50 ppm.

The method for forming the suture yarn from the PGA polymer in accordance with the present invention features three primary processing steps, namely:

1. Forming individual filaments
2. Combining the filaments to form a multi-filament suture yarn
3. Jet entanglement of the yarn.

1. Forming Individual Filaments

Figure 1:
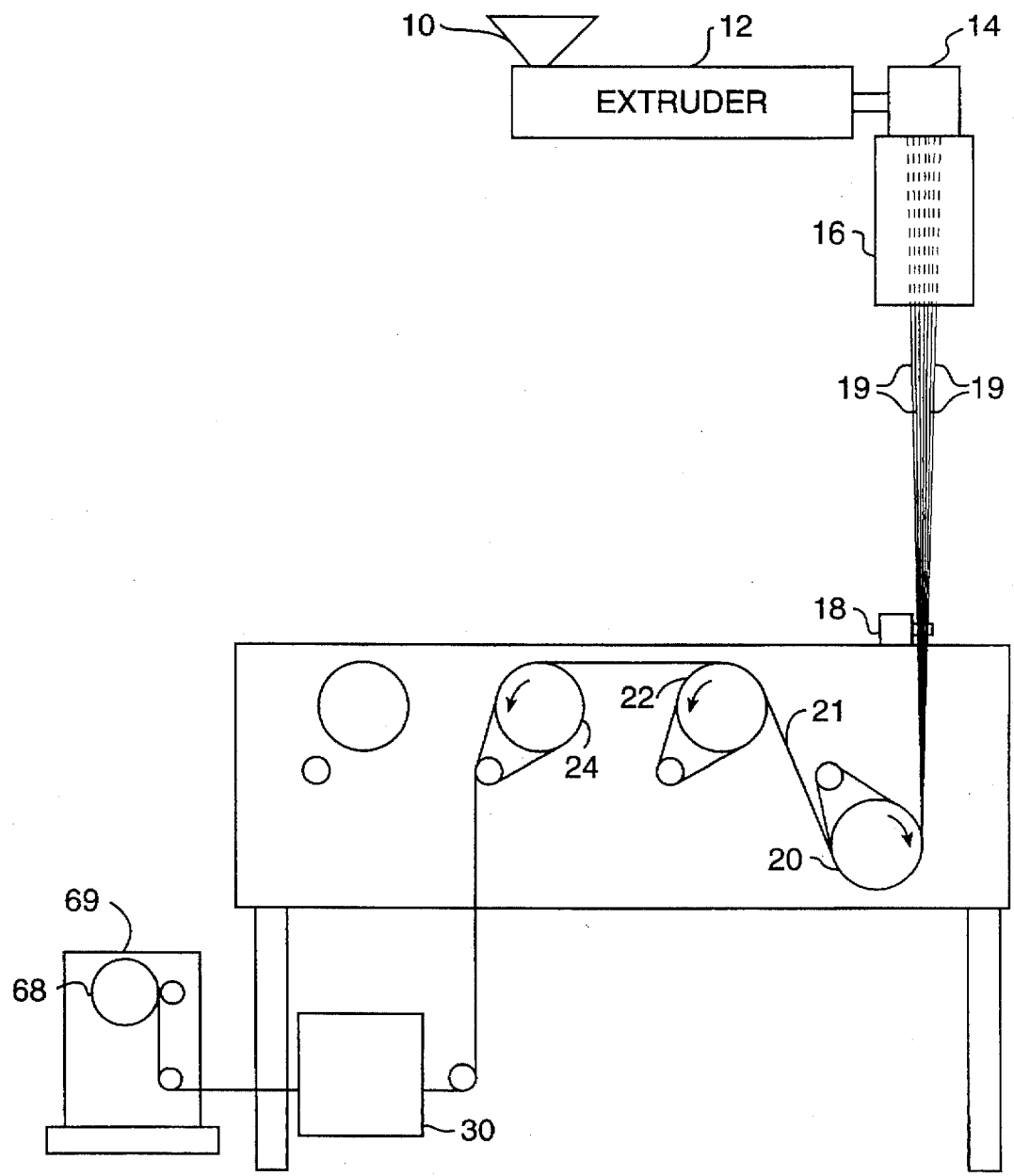
FIG. 1 is a schematic diagram of a spin-draw extruder used in accordance with the present invention.
Figure 2:
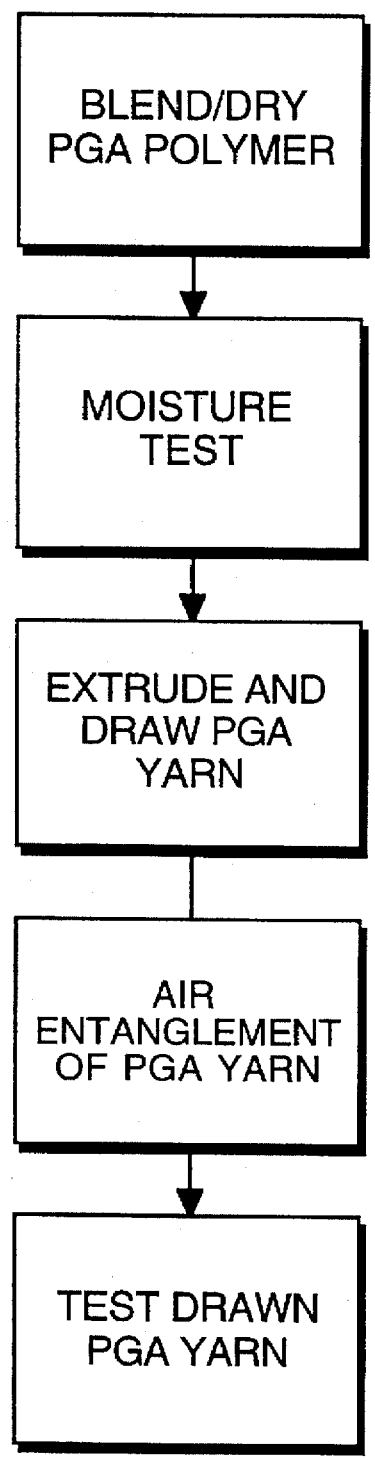
FIG. 2 is a flow diagram of a method of forming PGA filaments in accordance with the present invention.
Figure 3:
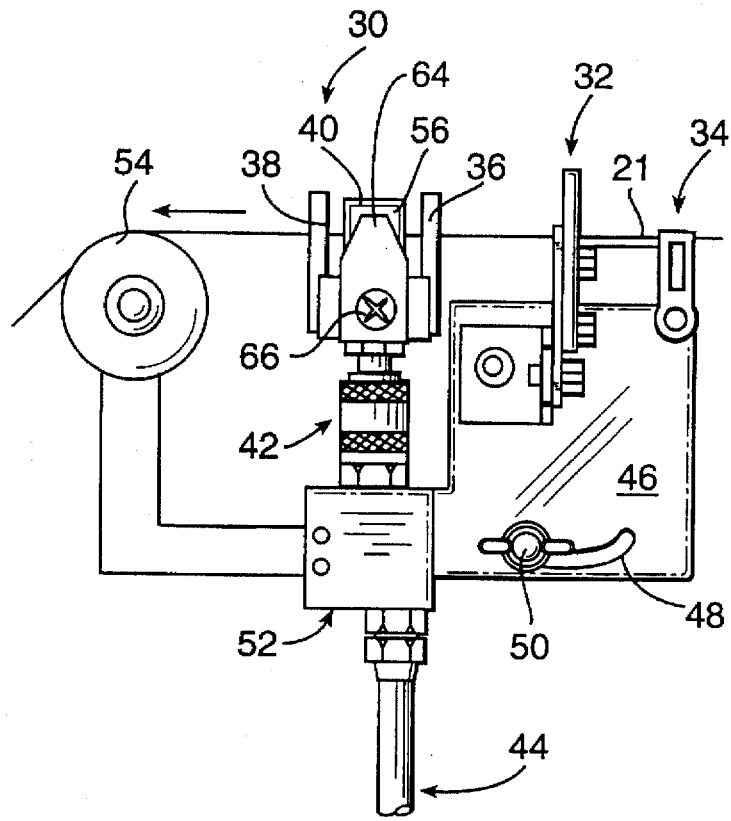
FIG. 3 is a side elevational view of a jet entanglement apparatus for processing the suture filaments in accordance with the present invention.
Figure 4:
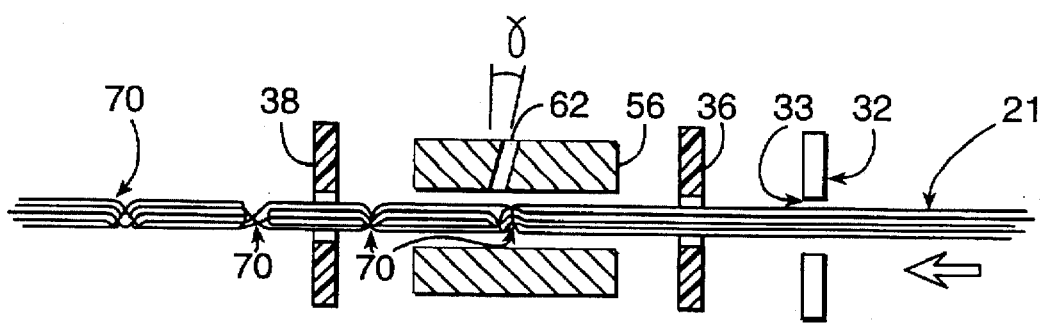
FIG. 4 is a sectional plan view of part of the air jet entanglement apparatus in accordance with the present invention.

Individual filaments fabricated from the PGA polymer resin are preferably melt extruded using a spin draw process. FIG. 1 shows a spin draw extrusion apparatus for forming the PGA filaments. With reference to FIG. 1 and the flow chart in FIG. 2, a dry PGA polymer, preferably having a moisture content no greater than 50 ppm, is fed into a hopper 10, extruded through a melt extruder 12 and formed into filaments by a spin head 14 containing filtration media and a spinneret. In one suitable example, a ¾ diameter, 20:1 l/d extruder is used to form the individual filaments, and is operated at a temperature of 250° C. The formed filaments are then passed through a hot collar 16 and are quenched in air as they drop from the hot collar.

2. Combining Filaments to Form a Multi-Filament Yarn

The number of filaments used to form a yarn depends on the overall denier of the suture yarn and whether the yarn is to be incorporated into a sheath or core.

After quenching, the individual filaments 19 are passed through a finish applicator 18 and then over a series of godets 20, 22 and 24 for drawing and relaxing the filaments. The finish applicator applies a spin finish solution to the filaments to assist in subsequent processing. The spin finish solution comprises a lubricating agent, e.g., mineral oil, an anti-static agent, such as sorbitan monolaurate, and a solvent, e.g., xylene. Xylene is a non-aqueous carrier and thus will not break down the PGA filaments. Of course, the spin finish is washed and rinsed or otherwise removed from the suture yarns after processing is complete.

As the treated filaments are passed over the godets 20, 22 and 24, the filaments are combined in a parallel contiguous arrangement to form a yarn 21. A tension is applied to the yarn as it passes over the godets to draw the yarn to the desired draw ratio. In one example, godet 20 takes up 2000 feet/minute (fpm) of yarn and is not heated, godet 22 is heated to 58° C. and operated to take up 2005 feet of yarn per minute, and godet 24 is heated to 110° C. and takes up 9000 fpm of yarn. A draw ratio of approximately 4.5× is achieved by operating the godets at these speeds, although the preferred range of draw ratio can be from 3 to 5×.

Filaments extruded for use in sheath or core construction preferably have a denier of between 0.2 to 6.0 denier, more preferably between 1.5 to 3.0 denier and ideally 2.2 denier. Sheath filaments desirably have a low denier to maintain smooth surface characteristics. Core filaments, on the other hand, may have a higher denier, especially for sutures with a high overall denier.

The preferable range of denier of the yarn is shown in Table 1.

TABLE 1

| Filaments | Denier Range | |
|---|---|---|
| | Minimum | Maximum |
| 7 | 14.5 | 16.3 |
| 16 | 33.1 | 37.3 |
| 21 | 43.4 | 49.0 |
| 28 | 57.9 | 65.3 |
| 35 | 72.4 | 81.6 |

The resulting yarn suitable for use to manufacture PGA braid preferably has a tenacity of at least 6.0 gpd and a breaking elongation between 15% and 40%.

3. Jet Entanglement of the Multi-Filament Yarn

As the yarn leaves the last godet 24 it proceeds to a jet entanglement apparatus 30 shown in block outline in FIG. 1 and in detail in FIGS. 3, 4, 5A and 5B.

In jet entanglement, a fluid is forced at elevated pressure into a chamber through which the multi-filament yarn is passed. The fluid is preferably air or some other gas. The turbulence of the gas causes the filament to entangle or intermingle in the area impinged by the jet. The movement of the yarn and the size of the chamber interact to create turbulent pulsations which entangle the filaments together.

Therefore, even with a constant pressure air supply, the yarn can exit the chamber with discrete regularly spaced apart areas of entanglement alternating with non-entangled areas. The entangled portions are retained by the yarn through subsequent processing steps. As will be appreciated, jet entanglement of the yarn achieves many of the same features of twisting the yarn but at a much higher speed and with a simpler process, thus reducing the costs associated with combining the individual filaments.

With reference to FIGS. 3, 4, 5A and 5B, the air jet entanglement apparatus 30 comprises a slub catcher 32, eyelets 34, 36 and 38, support frame 40, and quick release connector 42. The entangler also includes an air supply line 44 and a mounting plate 46 for supporting the entanglement device. The mounting plate includes an adjustment slot 48 with adjustment wing nut 50, support box 52, roller 54 and entanglement body 56.

Figure 5A:
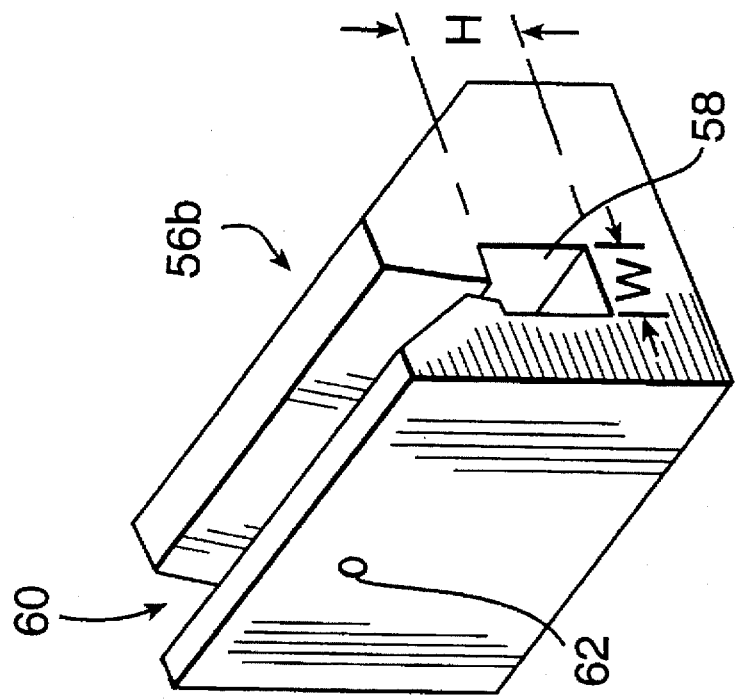
FIGS. 5A and 5B are perspective views of air jet entanglement chambers in accordance with the present invention.
Figure 5B:
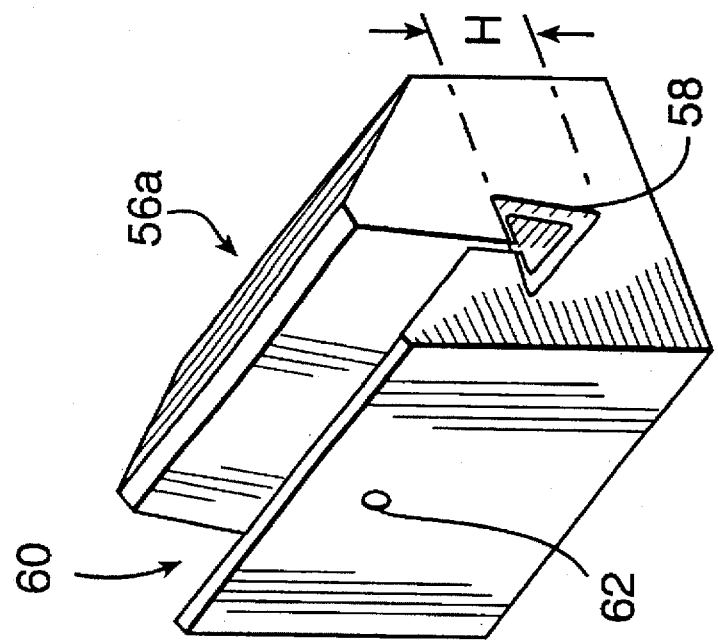

The entanglement body 56 is preferably fabricated as an integral single piece from a hard, durable material such as tungsten carbide, ceramic coated steel, or solid ceramic. As best seen in FIGS. 5A and 5B, the entanglement body is formed to have a chamber 58 extending lengthwise along the moving path of the threadline in which the entanglement takes place, and a threading slot 60 to facilitate easy threading of the suture yarn within the chamber. The chamber 58 can be triangular or rectangular in cross-section to facilitate turbulence.

The height H of the triangular chamber 58 in FIG. 5A, i.e., the distance from the base to the apex of the triangular cross-section, is preferably from about 2.0 millimeters to about 5.0 millimeters, and more preferably between 2.3 and 4.3 millimeters. The rectangular chamber 58 in FIG. 5B preferably has a height H of approximately 3.1 millimeters and a width W of approximately 1.1 millimeter. The preferred length of the chamber shown in FIG. 5B is approximately 25 millimeters. Air or other suitable gas is introduced into the chamber through an orifice 62, which may be oriented at an angle γ from a line perpendicular to the longitudinal path of the threadline. Angle γ can be from about 0° to about 15°. The diameter of the orifice can range from about 1 to 3 millimeters, and more preferably from about 1 to 1.5 millimeters. The air is introduced into the chamber at a preferred pressure of about 80 to 100 psi, although a range of about 10 to 100 psi is acceptable.

The entanglement body 56 is secured to the support frame 40 by a locking plate 64 and locking screw 66. Quick release connector 42 for the air supply line 44 is secured to the support block 52 and, in turn, supports the support frame 40 and allows for consistent and precise positioning of the entanglement body between eyelets 36 and 38. Of course, the entanglement body can be of any of the various configurations and dimensions suitable for the suture entangling process of the present invention.

With reference back again to FIGS. 1, 3 and 4, after suture yarn 21 passes over godet 24, it is then passed through eyelet 34, slot 33 in the slub catcher 32, through eyelet 36 and into chamber 56 at a preferred speed of up to about 9000 fpm. Air is injected from orifice 62 at approximately 80 to 100 psi and preferably at an angle γ of about 5°. The turbulence is characterized by pulsations, i.e., discrete impingements of air, on the suture yarn to produce impingements about, for example, every 1 cm to 4 cm. A slight tension of between 0.05 to 0.10 grams per denier (gpd) is applied to the yarn as it is drawn through the entangler. After exiting from chamber 56, the entangled yarn passes through eyelet 38, around roller 54, and onto a take-up spool 68 on winder 69 (see FIG. 1).

Subsequent processing of the entangled yarn may entail combining it with other entangled yarns and then twisting or braiding the combined yarns. Sutures can be formed with yarns comprising a separately constructed core around which sheath yarns are braided. In one embodiment, 3 to 7 air entangled yarns are individually fed into a center of a structure as it is being braided to compose the core. The 3 to 7 yarns can also be plied or twisted in a separate operation to form a core yarn. Alternatively, the need to ply multiple yarns can be eliminated by spinning large denier yarns having hundreds of filaments. The large denier yarns, on the order of from about 100 to about 1000 denier, are jet entangled in accordance with the invention.

On the other hand, sheath yarns do not need to be plied. For example, about 4 to 36 sheath yarns may be braided around a constructed core to form the finished suture. Alternatively, the finished suture may be braided with sheath yarns only and thus without a core.

Spin drawing a PGA polymer to form surgical filaments and subsequently processing the filament yarn using an air entangler offers many advantages over conventional medical suture forming methods. For example, spin drawing a PGA polymer significantly increases production over the conventional two-step extrusion method of forming suture filaments. Moreover, using a jet entangler to entangle the yarn eliminates the need for a twisting operation of the individual filaments and the accompanying capital costs of twisting equipment and facilities, resulting in lower production costs.

Another advantage of jet entanglement is that yarn processability is improved and breakage of filaments is reduced. Even if the filament breaks it can only strip back as far as the next closest impingement or entangled area, which is generally no more than about 1 to 4 centimeters. In addition, air entanglement tends to imbed broken ends of filaments within the suture yarn, reducing the likelihood that the broken filaments will not accumulate during further processing. These results are especially important when the individual filaments possess a low denier, e.g., a denier less than 2. Therefore, another related advantage of employing jet entanglement is that it enables the suture to be made from filaments of low denier at a low defect rate. Use of lower denier filaments, as discussed above, is desirable because lower denier filaments result in a smoother suture.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A method of forming absorbable, biocompatible suture filaments, comprising the steps of:

melt extruding a bioabsorbable polymer to form a plurality of surgical filaments; and drawing the filaments to form drawn filaments, wherein the melt extruding and drawing occur in a single continuous step.

2. A method of forming absorbable, biocompatible suture filaments, comprising the steps of:

melt extruding a bioabsorbable polymer to form a plurality of surgical filaments;

drawing the filaments in a continuous step to form drawn filaments; and treating extruded filaments with a finishing solution before drawing the filaments, the finishing solution having a lubricating agent and an anti-static agent in a non-aqueous carrying fluid.

3. A method according to claim 1, wherein the drawing step uses a plurality of rotatable godets operated at different speeds to draw the filaments.

4. A method according to claim 1, wherein the bioabsorbable polymer is poly(glycolic acid).

5. A method according to claim 2, wherein the non-aqueous carrying fluid is xylene.

6. A method of forming an absorbable, biocompatible suture yarn, comprising the steps of:

melt extruding a bioabsorbable polymer to form a plurality of surgical filaments;

drawing the extruded filaments in a step continuous with the melt extruding step;

combining the drawn filaments into a parallel contiguous arrangement to form a yarn; and securing the filaments together to stabilize the yarn.

7. A method of forming an absorbable, biocompatible suture yarn, comprising the steps of:

melt extruding a bioabsorbable polymer to form a plurality of surgical filaments;

drawing the extruded filaments in a continuous step;

combining the drawn filaments into a parallel contiguous arrangement to form a yarn;

securing the filaments together to stabilize the yarn; and treating extruded filaments with a finishing solution before drawing the filaments, the finishing solution having a lubricating agent and an anti-static agent in a non-aqueous carrying fluid.

8. A method according to claim 7, wherein the non-aqueous carrying fluid is xylene.

9. A method of forming an absorbable, biocompatible suture yarn, comprising the steps of:

melt extruding a bioabsorbable polymer to form a plurality of surgical filaments;

drawing the extruded filaments in a continuous step;

combining the drawn filaments into a parallel contiguous arrangement to form a yarn;

securing the filaments together to stabilize the yarn; and entangling the yarn in the securing step.

10. A method according to claim 9, wherein the entangling step includes the steps of threading the combined filaments through an entanglement chamber and impinging fluid upon the filaments to form spaced entangled portions in the yarn.

11. A method according to claim 9, wherein the entangling step impinges air upon the filaments to form spaced entangled portions in the yarn.

12. A method according to claim 6, wherein the drawing step uses a plurality of rotatable godets operated at different speeds to draw the filament.

13. A method according to claim 6, wherein the bioabsorbable polymer is poly(glycolic acid).

14. A method according to claim 6, further comprising the step of entangling the yarn in the securing step.

15. A method according to claim 14, wherein the entangling step includes the steps of threading the combined filaments through an entanglement chamber and impinging fluid upon the filaments to form spaced entangled portions in the yarn.

16. A method according to claim 14, wherein the entangling step impinges air upon the filaments to form spaced entangled portions in the yarn.

* * * * *

UNITED STATES PATENT AND TRADEMARK OFFICE
CERTIFICATE OF CORRECTION

PATENT NO. : 5,688,451

DATED : November 18, 1997

INVENTOR(S) : Hutton

It is certified that error appears in the above-identified patent and that said Letters Patent is hereby corrected as shown below:

COLUMN 1:

Line 4, "continuation-in-part" should read --continuation--.

Signed and Sealed this

Sixteenth Day of February, 1999

Attest:

*Acting Commissioner of Patents and Trademarks*

Attesting Officer